United States Patent
Chowaniec et al.

(10) Patent No.: US 9,022,211 B2
(45) Date of Patent: *May 5, 2015

(54) KNOTLESS ENDOSTITCH PACKAGE

(71) Applicant: Covidien LP, Mansfield, MA (US)

(72) Inventors: Matthew Chowaniec, Middletown, CT (US); David Kirsch, Madison, CT (US)

(73) Assignee: Covidien LP, Mansfield, MA (US)

( * ) Notice: Subject to any disclaimer, the term of this patent is extended or adjusted under 35 U.S.C. 154(b) by 197 days.

This patent is subject to a terminal disclaimer.

(21) Appl. No.: 13/632,402

(22) Filed: Oct. 1, 2012

(65) Prior Publication Data

US 2013/0026053 A1    Jan. 31, 2013

Related U.S. Application Data

(63) Continuation of application No. 12/775,553, filed on May 7, 2010, now Pat. No. 8,292,067.

(60) Provisional application No. 61/185,432, filed on Jun. 9, 2009.

(51) Int. Cl.
*A61B 17/06* (2006.01)
*A61B 17/062* (2006.01)

(52) U.S. Cl.
CPC ..... *A61B 17/06114* (2013.01); *A61B 17/06123* (2013.01); *A61B 17/0625* (2013.01); *A61B 2017/06142* (2013.01); *A61B 2017/06176* (2013.01)

(58) Field of Classification Search
USPC ........ 206/63.3, 339, 388, 409, 227, 570, 560, 206/338, 764–765, 557, 562–566, 438, 380, 206/382, 383, 574, 229, 310, 340–341; 220/528, 592.02, 735, 212
See application file for complete search history.

(56) References Cited

U.S. PATENT DOCUMENTS

| | | | |
|---|---|---|---|
| 2,615,565 A | | 10/1952 | Bower et al. |
| 3,376,973 A | * | 4/1968 | Granowitz et al. .......... 206/63.3 |
| 3,495,703 A | | 2/1970 | Calabrese |
| 3,749,238 A | * | 7/1973 | Taylor ........................... 206/227 |
| 3,972,418 A | | 8/1976 | Schuler et al. |
| 4,191,291 A | | 3/1980 | Brown |
| 4,424,898 A | | 1/1984 | Thyen et al. |

(Continued)

FOREIGN PATENT DOCUMENTS

| | | |
|---|---|---|
| DE | 2618662 | 3/1977 |
| WO | WO97/41780 | 11/1997 |
| WO | WO 97/41780 A1 | 11/1997 |

OTHER PUBLICATIONS

European Search Report for EP 10251058.3-2310 date of completion is Nov. 8, 2011 (3 pages).

*Primary Examiner* — Anthony Stashick
*Assistant Examiner* — Robert Poon (57) ABSTRACT

Various embodiments of suture packages are disclosed to provide a surgical needle, having an associated length of suture material, to a surgical suturing instrument. The disclosed suture packages generally include a body portion having a needle supplying loading unit mounted thereon. Various methods of affixing the loading unit to the body portion are disclosed. The body portion defines a suture tray and a cover is provided to secure a suture within the suture tray. A securing ring is provided to secure the cover to the body portion.

11 Claims, 9 Drawing Sheets

(56) References Cited

U.S. PATENT DOCUMENTS

| | | | |
|---|---|---|---|
| 4,572,363 A | 2/1986 | Alpern | |
| 4,961,498 A | 10/1990 | Kalinski et al. | |
| 4,967,902 A | 11/1990 | Sobel et al. | |
| 5,052,551 A | 10/1991 | Cerwin et al. | |
| 5,056,658 A | 10/1991 | Sobel et al. | |
| 5,131,534 A | 7/1992 | Brown et al. | |
| 5,154,283 A | 10/1992 | Brown | |
| 5,165,217 A | 11/1992 | Sobel et al. | |
| 5,205,407 A | 4/1993 | Tu | |
| 5,213,210 A | 5/1993 | Cascio et al. | |
| 5,228,565 A | 7/1993 | Sinn | |
| 5,230,424 A | 7/1993 | Alpern et al. | |
| 5,236,083 A | 8/1993 | Sobel et al. | |
| 5,249,671 A * | 10/1993 | Sinn | 206/63.3 |
| 5,249,673 A | 10/1993 | Sinn | |
| 5,271,495 A | 12/1993 | Alpern | |
| 5,284,240 A | 2/1994 | Alpern et al. | |
| 5,350,060 A | 9/1994 | Alpern et al. | |
| 5,392,903 A | 2/1995 | Sinn | |
| 5,462,162 A | 10/1995 | Kaplan et al. | |
| 5,472,081 A | 12/1995 | Kilgrow et al. | |
| 5,478,344 A | 12/1995 | Stone et al. | |
| 5,478,345 A | 12/1995 | Stone et al. | |
| 5,503,266 A * | 4/1996 | Kalbfeld et al. | 206/63.3 |
| 5,540,324 A * | 7/1996 | Knapp | 206/6.1 |
| D374,284 S | 10/1996 | Stone et al. | |
| D374,285 S | 10/1996 | DeFonzo et al. | |
| 5,575,382 A | 11/1996 | Sobel et al. | |
| D378,131 S | 2/1997 | Stone et al. | |
| 5,628,395 A | 5/1997 | Daniele et al. | |
| 5,655,652 A | 8/1997 | Sobel et al. | |
| 5,667,155 A | 9/1997 | Cerwin et al. | |
| 5,669,490 A | 9/1997 | Colligan et al. | |
| 5,728,107 A | 3/1998 | Zlock et al. | |
| 5,733,293 A * | 3/1998 | Scirica et al. | 606/144 |
| 5,755,729 A | 5/1998 | de la Torre et al. | |
| 5,813,564 A | 9/1998 | Luo | |
| 5,814,069 A | 9/1998 | Schulze et al. | |
| 5,833,055 A | 11/1998 | Cerwin et al. | |
| 5,887,706 A | 3/1999 | Pohle et al. | |
| 5,906,273 A | 5/1999 | Pohle et al. | |
| 5,941,430 A * | 8/1999 | Kuwabara | 223/109 R |
| 5,960,982 A * | 10/1999 | Perlis et al. | 220/574 |
| 6,016,905 A * | 1/2000 | Gemma et al. | 206/63.3 |
| 6,047,815 A | 4/2000 | Cerwin et al. | |
| 6,076,659 A | 6/2000 | Baumgartner et al. | |
| 6,135,272 A | 10/2000 | Sobel et al. | |
| 6,260,699 B1 | 7/2001 | Kaplan et al. | |
| 6,464,071 B2 | 10/2002 | Baumgartner | |
| 6,464,077 B1 * | 10/2002 | Liu | 206/388 |
| 6,481,568 B1 | 11/2002 | Cerwin et al. | |
| 6,533,112 B2 | 3/2003 | Warnecke | |
| 6,644,469 B2 | 11/2003 | Alpern | |
| 6,887,259 B2 | 5/2005 | Lizardi | |
| 8,292,067 B2 * | 10/2012 | Chowaniec et al. | 206/63.3 |
| 2004/0050721 A1 | 3/2004 | Roby et al. | |
| 2005/0035007 A1 | 2/2005 | Kennedy et al. | |
| 2005/0077197 A1 | 4/2005 | Detruit et al. | |
| 2006/0226031 A1 | 10/2006 | Kennedy et al. | |
| 2007/0029215 A1 * | 2/2007 | Martinez et al. | 206/223 |
| 2007/0227914 A1 | 10/2007 | Cerwin et al. | |
| 2007/0256945 A1 | 11/2007 | Kennedy et al. | |
| 2008/0185752 A1 | 8/2008 | Cerwin et al. | |
| 2009/0139890 A1 | 6/2009 | Hatcher | |
| 2009/0205987 A1 | 8/2009 | Kennedy et al. | |
| 2009/0250356 A1 | 10/2009 | Kirsch et al. | |
| 2010/0084294 A1 | 4/2010 | Kirsch et al. | |
| 2010/0140115 A1 | 6/2010 | Kirsch | |

* cited by examiner

Fig. 11

KNOTLESS ENDOSTITCH PACKAGE

CROSS REFERENCE TO RELATED APPLICATION

This application is a continuation of U.S. application Ser. No. 12/775,553 filed May 7, 2010, now U.S. Pat. No. 8,292,067, which claims benefit to and priority from U.S. Provisional Application Ser. No. 61/185,432, filed Jun. 9, 2009, the disclosure of which is incorporated herein by reference in its entirety.

BACKGROUND

1. Technical Field

The present disclosure relates to suture packages for supplying a surgical needle, having an associated length of suture material attached thereto, to a surgical suturing apparatus. More particularly, the present disclosure relates to a suture package having a circular body portion defining a suture tray for receipt of the length of suture material and a loading unit affixed to the circular body portion for supporting the surgical needle relative to the surgical suturing apparatus.

2. Background of Related Art

During various surgical procedures it is often necessary to manipulate a surgical needle, having a length of suture material attached thereto, with a surgical suturing apparatus. This is particularly true in minimally invasive surgical procedures wherein the surgery is performed through a small incision or port allowing access to a body cavity.

Various forms of packaging or devices have been developed to provide the surgical needle and an associated length of suture material to the surgical suturing apparatus. These packages or devices typically hold the surgical needle loosely within the packaging and bend, or wrap, the length of suture material within the packaging to conserve space. Often the length of suture material is wrapped into a figure eight configuration. Alternatively, the length of suture material may be wrapped around a spool positioned within the packaging.

In a particular application, a double ended surgical needle is used in conjunction with the surgical suturing apparatus. The double ended surgical needle is alternately secured within the jaws of the surgical suturing apparatus, specifically within small holes formed within the jaws. In order to load the surgical needle within the jaws of the suturing apparatus, the jaws of the suturing apparatus and, specifically, the holes formed therein, must be precisely aligned over opposite ends of the double ended surgical needle. Specialized loading units are known and support the double ended surgical needle in a position for alignment with the jaws of a surgical suturing apparatus.

Additionally, some surgical procedures are best performed with the use of a barbed length of suture material having a loop at one end thereof. After suturing the appropriate tissue, the surgical needle is passed through the loop such that the barbs in the length of suture material engage the interior of the loop to lock the suture in place about the tissue. Due to the presence of barbs, which tend to engage or foul with each other, it is often not desirable to wrap a length of suture material within compact packaging such that it passes back over itself.

Therefore, a need exists for a suture package which is capable of precisely positioning a surgical needle for receipt by a surgical suturing apparatus. There is also a need for a suture package accommodating a barbed length of suture material without risk of the barbs entangling themselves.

SUMMARY

There is disclosed a suture package containing a surgical needle and a length of suture material for use with a surgical suturing apparatus. The suture package generally includes a body portion defining a suture tray and a loading unit located within the confines of the body portion. The suture tray supports a length of suture material and the loading unit supports a surgical needle affixed to the length of suture material. The loading unit is secured to the body portion. The body portion includes a tunnel extending inwardly toward the center of the body portion and the loading unit is secured to the tunnel. The loading unit includes tabs and the tunnel includes slots such that the loading unit is secured to the tunnel by engagement of the tabs within the slots.

In one embodiment, a plate is positioned over an opening in the tunnel and the loading unit is secured to the plate.

The suture package additionally includes a cover overlying the tray defined by the body portion. The cover is secured to the body portion and includes an opening such that the loading unit is exposed through the opening in the cover. A fixture is positionable about the cover and engageable with the body portion to secure the cover to the body portion.

There is also disclosed a suture package having a circular body portion defining a suture tray and a loading unit on the circular body portion. The suture tray supports a length of suture material and the loading unit supports a surgical needle affixed to the length of suture material. The length of suture material is a length of knotless suture material.

In this embodiment the circular body portion includes a radially inwardly directed tunnel such that the suture tray is generally U-shaped. The loading unit is secured to the tunnel. A plate having slots is provided and is located on the tunnel. The loading unit includes tabs engageable within the slots to secure the loading unit to the tunnel.

A cover overlies the tray defined by the circular body portion. The cover is secured to the circular body portion and includes an opening such that the loading unit is exposed through the opening in the cover. A ring is provided and is positionable about the cover and engageable with the circular body portion to secure the cover to the circular body portion.

There is further disclosed a suture package having a circular body portion defining a circular suture tray and a loading unit mounted on the circular body portion. The suture tray supports a length of suture material and the loading unit supports a surgical needle affixed to the length of suture material.

In this embodiment, the loading unit is mounted on a post extending from the center of the circular suture tray.

DESCRIPTION OF THE DRAWINGS

Various embodiments of the presently disclosed knotless suture package are disclosed herein with reference to the drawings, wherein.

DETAILED DESCRIPTION OF EMBODIMENTS

Embodiments of the presently disclosed knotless suture package will now be described in detail with reference to the drawings wherein like numerals designate identical or corresponding elements in each of the several views. As is common in the art, the term "proximal" refers to that part or component closer to the user or operator, i.e., surgeon or physician, while the term "distal" refers to that part or component further away from the user.

Figure 1:
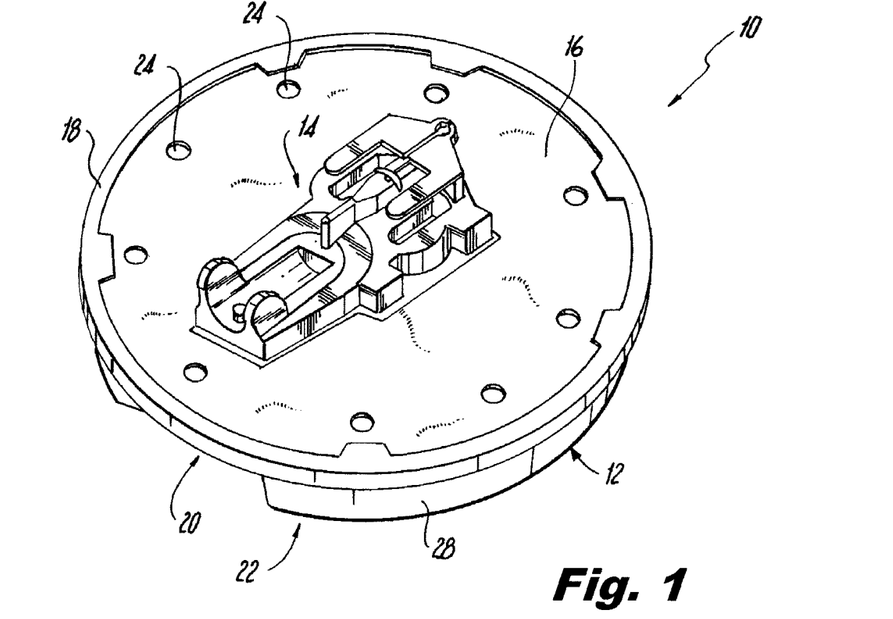
FIG. 1 is a perspective view, taken from the top, of one embodiment of a knotless suture package.
Figure 2:
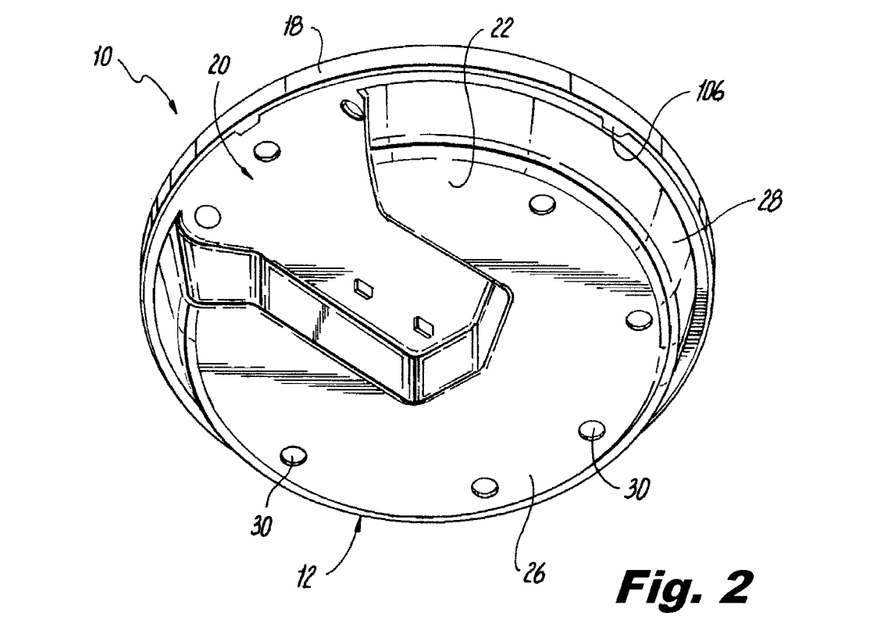
FIG. 2 is a perspective view, taken from the bottom, of the knotless suture package of FIG. 1.

Referring to FIGS. 1 and 2, disclosed is a suture package 10 for use with a surgical suturing apparatus (not shown). Suture package 10 generally includes a circular body portion 12 having a loading unit 14 mounted on circular body portion 12. It should be noted that loading unit 14 is positioned within the confines of circle body portion 12. A cover 16 overlies circular body portion 12 and is secured to circular body portion 12 by a securing fixture or ring 18. While circular body portion 12 is disclosed as being circular it is contemplated that circular body portion 12 may have other shapes, such as, for example, oval, square, rectangular, triangular, asymmetric to be ergonomically optimized, etc. In one embodiment, the body portion is circular for ease of suture loading and winding. Body portion 12 includes a tunnel 20 and a U-shaped suture tray or suture tray 22. Tunnel 20 is provided for supporting loading unit 14 on body portion 12 while suture tray 22 is provided to receive a length of barbed suture 34 as described in more detail hereinbelow.

As best shown in FIG. 1, cover 16 is provided with a plurality of cover holes 24 which allow for the passage of sterilization gases into suture tray 22 to sterilize the suture. Additionally or alternatively, cover 16 may be formed from a permeable material to allow for the passage of sterilization gases. As will be discussed further below, holes 24 are positioned to align with a plurality of holes 30 formed in a body base portion 26 and are configured to receive winding pegs (not shown) from a winding device (not shown). Further, cover 16 may be formed from a transparent or semitransparent material to allow the surgeon to view the length of suture therein and confirm that the suture has not become tangled upon itself prior to use.

With reference to FIG. 2, body portion 12 includes a body portion base 26 and a circular sidewall 28. Body portion base 26 and circular sidewall 28 define suture tray 22. As with cover 16, body portion base 26 is provided with a plurality of holes 30 which allow for the passage of sterilization gases into suture tray 22. As discussed above, holes 30 align with holes 24 formed in cover 16 and are configured to receive winding pegs (not shown) from a winding device (not shown). Additionally, while not specifically shown, it is contemplated that circular sidewall 28 may also be provided with holes for the passage of sterilization gases.

Figure 3:
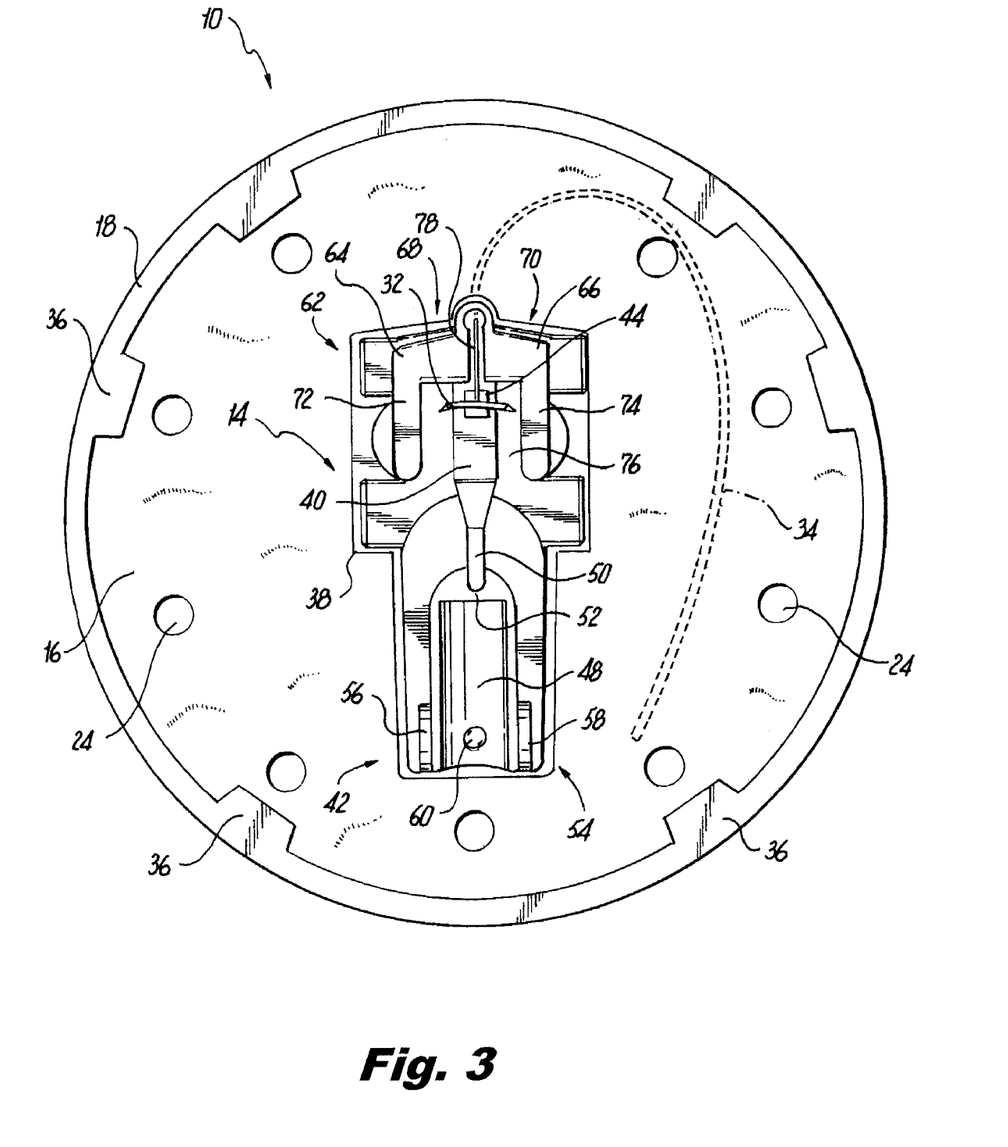
FIG. 3 is a top plan view of the knotless suture package of FIG. 1, with part of a knotless suture shown in phantom.

Referring now to FIG. 3, loading unit 14 is provided to supply a surgical needle such as, for example, double pointed surgical needle 32 to a surgical suturing instrument. A length of barbed suture material such as, for example, suture 34 is affixed to surgical needle 32 and extends into suture tray 22. While not specifically shown, a loop may be formed at the free end of suture 34 for passage of surgical needle 32 therethrough. Additionally, barbs formed on suture 34 may engage the loop thus allowing suture 34 to be self locking. As shown, inwardly directed tabs 36 on ring 18 assist in retaining cover 16 over body portion 12.

Figure 4:
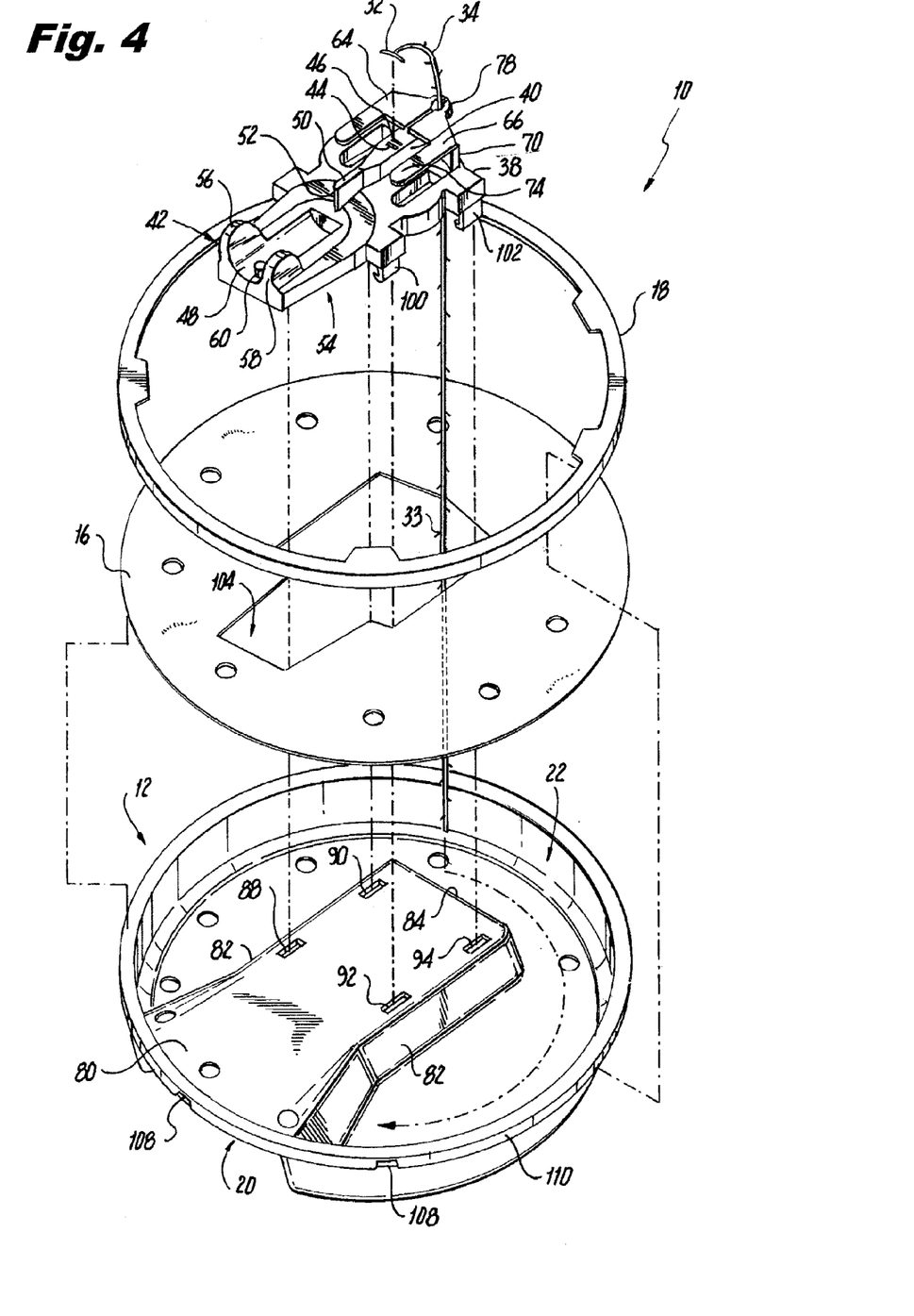
FIG. 4 is an exploded perspective view of the knotless suture package of FIG. 1.
Figure 5:
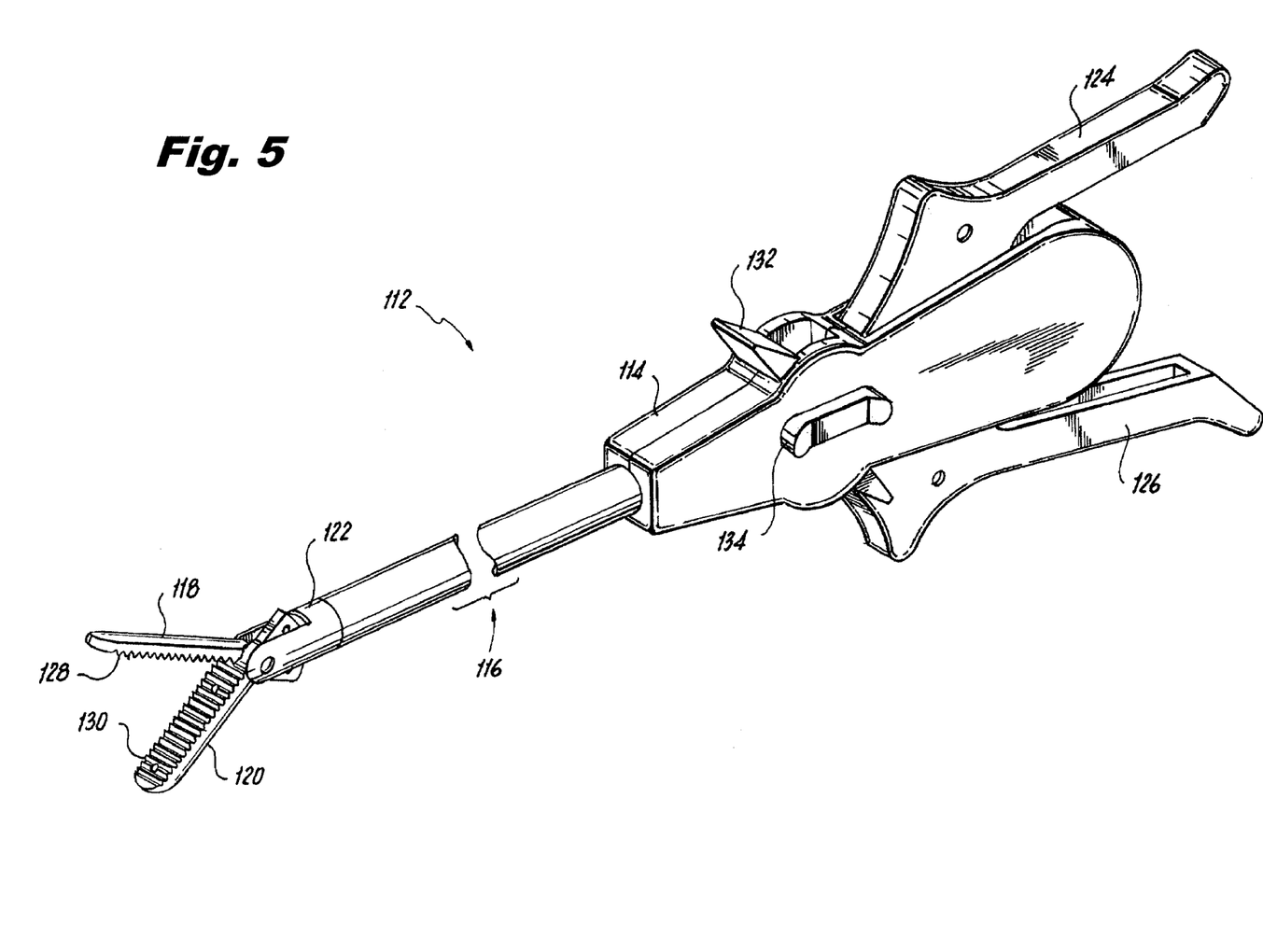
FIG. 5 is a perspective view of a surgical suturing apparatus designed for use with a double ended surgical needle.

With reference to FIGS. 3 and 4, the details of loading unit 14 will now be described. As noted here in above, loading unit 14 is provided to support and supply double ended needle 32 to a surgical suturing apparatus 112 (FIG. 5). Loading unit 14 includes a base 38 which may be affixed to body portion 12 or may be formed integrally with body portion 12. A needle support member 40 extends vertically upwardly from base 38 and is configured to support surgical needle 32 in an elevated position relative to base 38. This allows room for jaws of a surgical suturing apparatus 112 to be moved into engagement with surgical needle 32. Apparatus receiving structure 42 is provided on loading unit 14 to properly position the surgical suturing apparatus with respect to surgical needle 32.

A needle block 44 is provided on needle support member 40 to frictionally hold surgical needle 32 on needle support member 40. As best shown in FIG. 4, needle block 44 includes a needle notch 46 for frictional receipt of surgical needle 32.

Apparatus receiving structure 42 includes a recess 48, provided in base 38, for receipt of a distal end of the surgical suturing apparatus. A proximal end 50 of needle support member 40 forms an abutment surface 52 to limit the advancement of the surgical suturing apparatus within loading unit 14. Apparatus alignment structure 54 is additionally provided to guide surgical suturing apparatus within loading unit 14 and generally includes a pair of first and second side tabs 56 and 58 which are configured to align an elongate member of the surgical suturing apparatus properly relative to surgical needle 32. A support stud 60 is additionally provided within recess 48 and is configured to engage a recess formed within the elongate member of the surgical suturing apparatus.

Loading unit 14 is provided with blocking structure 62 in order to guide the jaws of the surgical suturing apparatus into engagement with surgical needle 32 and prevent removal of surgical needle 32 until surgical needle 32 has been fully grasped by the jaws of the surgical suturing instrument. Blocking structure 62 generally includes a first blocking member 64 and a second blocking member 66 extending from base 38 adjacent needle support member 40. First and second blocking members 64 and 66 include respective vertical supports 68 and 70 and L-shaped proximally extending arms 72 and 74 located above surgical needle 32. By positioning proximally extending arms 72 and 74 above surgical needle 32 room is provided for the jaws of the surgical instrument to pass under proximally extending arms 72 and 74 to surround and grasp surgical needle 32 in a manner described in more detail hereinbelow.

It should be noted herein, that first and second blocking members 64 and 66 and, specifically, proximally extending arms 72 and 74 prevent removal or lifting of surgical needle 32 from needle support member 40 until such time as surgical needle 32 has been properly grasped by the surgical suturing instrument and the jaws of the surgical suturing instrument are in a fully closed position. First and second proximally extending arms 72 and 74 define a proximal gap 76 (FIG. 3) therebetween which allows the fully closed jaws of the surgical suturing instrument to be lifted vertically to thereby remove surgical needle 32 from needle block 44. Likewise, a distal gap 78 is formed between first and second proximally extending arms 72 and 74 for passage of length of suture material 34. Distal gap 78 allows passage of length of suture material 34 into suture tray 22.

Figures 6, 7:
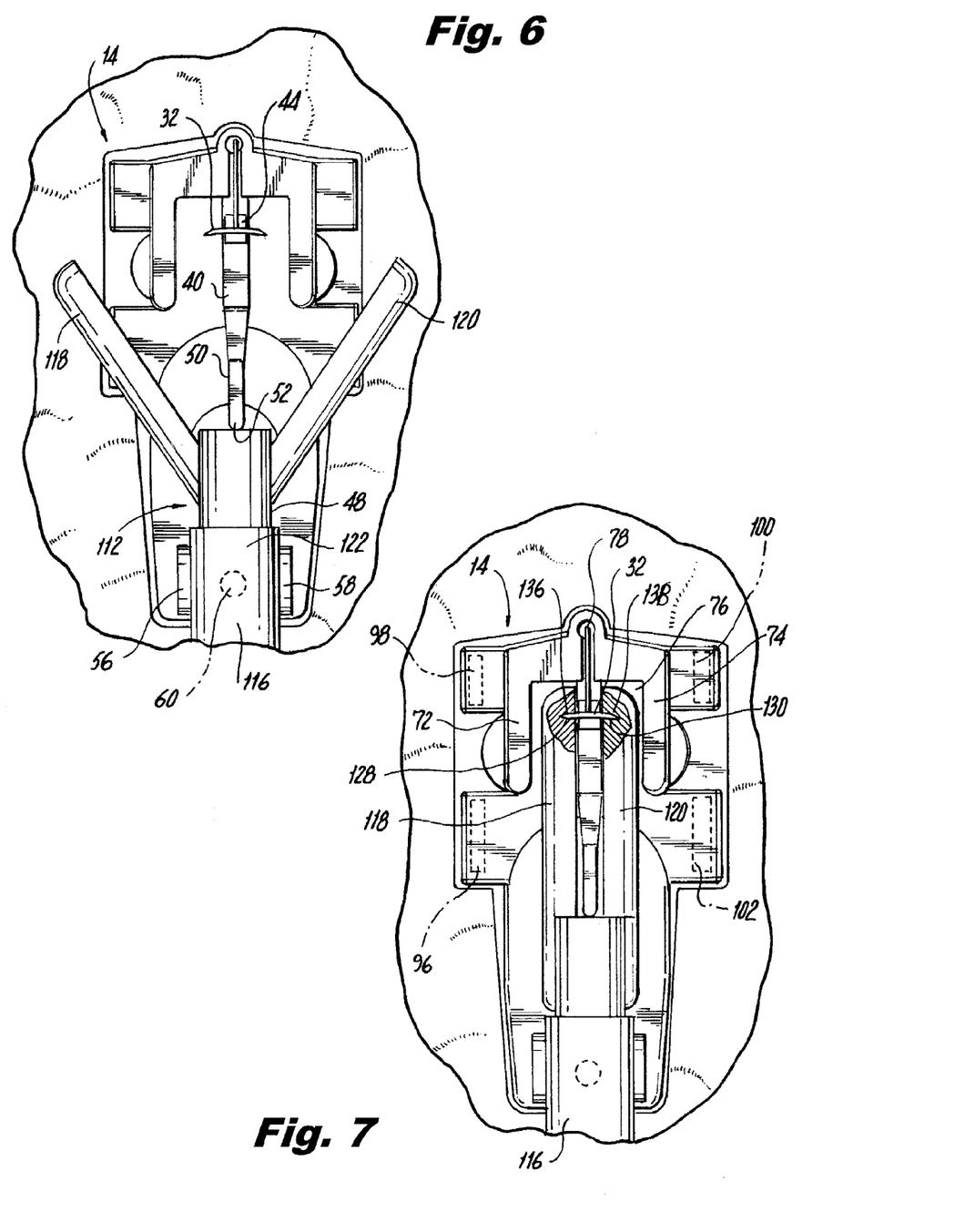
FIG. 6 is top view of the distal end of the surgical suturing apparatus positioned within a loading unit of the knotless suture package of FIG. 1.
FIG. 7 is a view similar to FIG. 6, partially shown in section, with jaws of the surgical suturing apparatus closed about a double ended surgical needle held in the loading unit.

Referring now specifically to FIG. 4, and as noted herein above, loading unit 14 is secured to body portion 12. Tunnel 20 generally includes a tunnel top 80 having side walls 82 and 84 and an end wall 86. Side walls 82 and 84, along with end wall 86, provided the generally U-shape to suture tray 22 within body portion 12. Slots 88, 90, 92 and 94 are formed in top 80. Slots 88, 90, 92 and 94 are configured to receive respective downwardly projecting tabs 96, 98, 100, 102 (FIG. 7, shown in phantom) on loading unit 14. This secures loading unit 14 to body portion 12. Thus, in this embodiment, loading unit 14 is secured to tunnel 20 formed in body portion 12. As shown, a cut out 104 is formed in cover 16 to accommodate loading unit 14 and the passage of length of suture material 34 from loading unit 14 into suture tray 22.

As noted herein above, ring 18 is provided to secure cover 16 to body portion 12. Specifically, inwardly directed tabs 106 formed on ring 18 (FIG. 2) engage notches 108 formed in a circumferential lip 110 formed in body portion 12 (FIG. 4).

Referring now to FIGS. 5-8, the use of a surgical suturing apparatus such as, for example, surgical suturing apparatus 112 to remove needle 32 and length of suture 34 from within suture package 10 will now be described. A particularly suitable surgical suturing apparatus 112 is disclosed in U.S. Pat. No. 5,728,107 entitled "SURGICAL SUTURING APPARATUS WITH LOADING MECHANISM", the entire disclosure of which is incorporated by reference herein. Although shown and described with respect to surgical suturing apparatus 112, the aspects for the present disclosure may be modified for use with other surgical devices.

Referring initially to FIG. 5, surgical suturing apparatus 112 generally includes a body portion 114 having an elongate tubular member 116 extending distally from body portion 114. A pair of needle grasping jaws, such as first and second jaws 118 and 120, is pivotally mounted on a distal end 122 of elongate tubular member 116. First and second jaws 118 and 120 are movable from an open position wherein first and second jaws 118 and 120 are substantially spaced apart to a closed position wherein first and second jaws 118 and 120 are substantially adjacent to each other. A pair of handles 124 and 126 is provided on body portion 114 to move first and second jaws 118 and 120 between the open and closed positions. Needle holding recesses 128 and 130 are formed within first and second jaws 118 and 120, respectively, to receive and engage the tissue penetrating tips of surgical needle 32. A toggle lever 132 is provided to alternately secure surgical needle 32 within one of first and second jaws 118 and 120. An override switch 134 is provided to secure surgical needle 32 within needle recesses 128 and 130 when first and second jaws 118 and 120 are in a closed positioned so as to enable surgical suturing apparatus 112 to remove surgical needle 32 from loading unit 14.

Referring now to FIG. 6, initially, surgical needle 32 is supported within needle block 44 in loading unit 14. Surgical suturing apparatus 112 is manipulated to position distal end 122 of elongate tubular member 116 within recess 48 formed in loading unit 14. Distal end 122 is retained within loading unit 14 by engagement with first and second side tabs 56 and 58. Distal end 122 is advanced distally within loading unit 14 until it engages abutment surface 52 formed on proximal end 50 of needle support member 40. Distal end 122 of elongate tubular member 116 is secured within loading unit 14 by engagement with support stud 60 provided within recess 48.

Referring now to FIGS. 5 and 7, handles 124 and 126 are actuated to move first and second jaws 118 and 120 from the open to the closed position. As first and second jaws 118 and 120 are moved to the closed position, a pair of tissue penetrating tips 136 and 138 enter needle recesses 128 and 130 formed in first and second jaws 118 and 120, respectively. Operation of toggle lever 132 and override switch 134 function to secure surgical needle 32 within first and second jaws 118 and 120.

Figure 8:
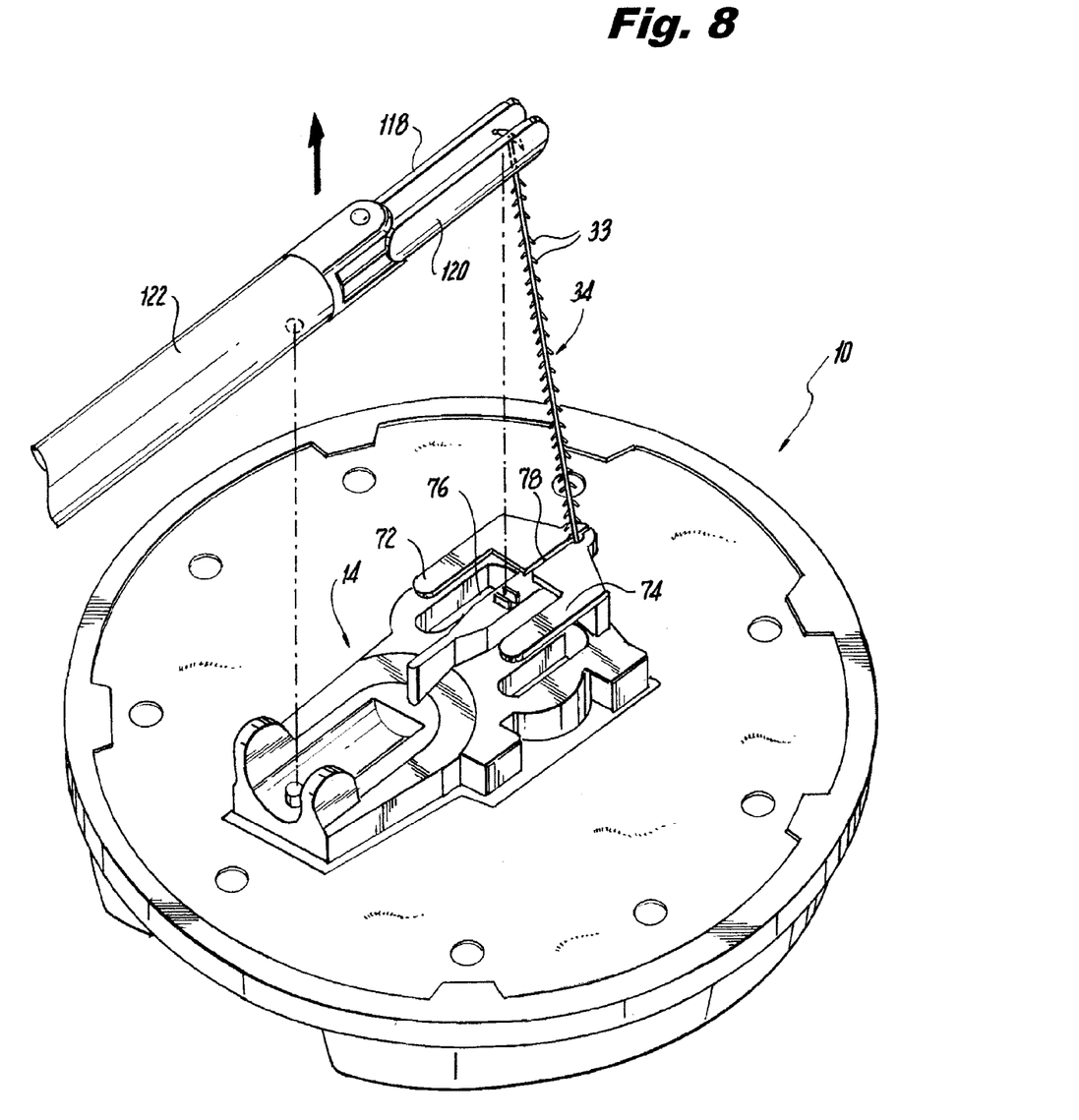
FIG. 8 is a view similar to FIG. 7 illustrating the removal of the double ended surgical needle and an attached length of knotless suture from the loading unit.

Referring now to FIGS. 7 and 8, as shown, when first and second jaws 118 and 120 are in the closed position they may be lifted upwardly through proximal gap 76 defined between first and second proximally extending arms 72 and 74. Additionally, length of suture material 34 is free to pass upwardly through distal gap 78. Continued lifting of elongate tubular member 122 will serve to draw length of suture material 34 out of suture tray 22 and pull length of suture material 34 free from suture package 10.

Thus, suture retainer 10 provides a safe and convenient method of supplying a suture assembly, including double ended surgical needle 32 having length of barbed suture material 34 attached thereto, to surgical suturing apparatus 112.

Figure 9:
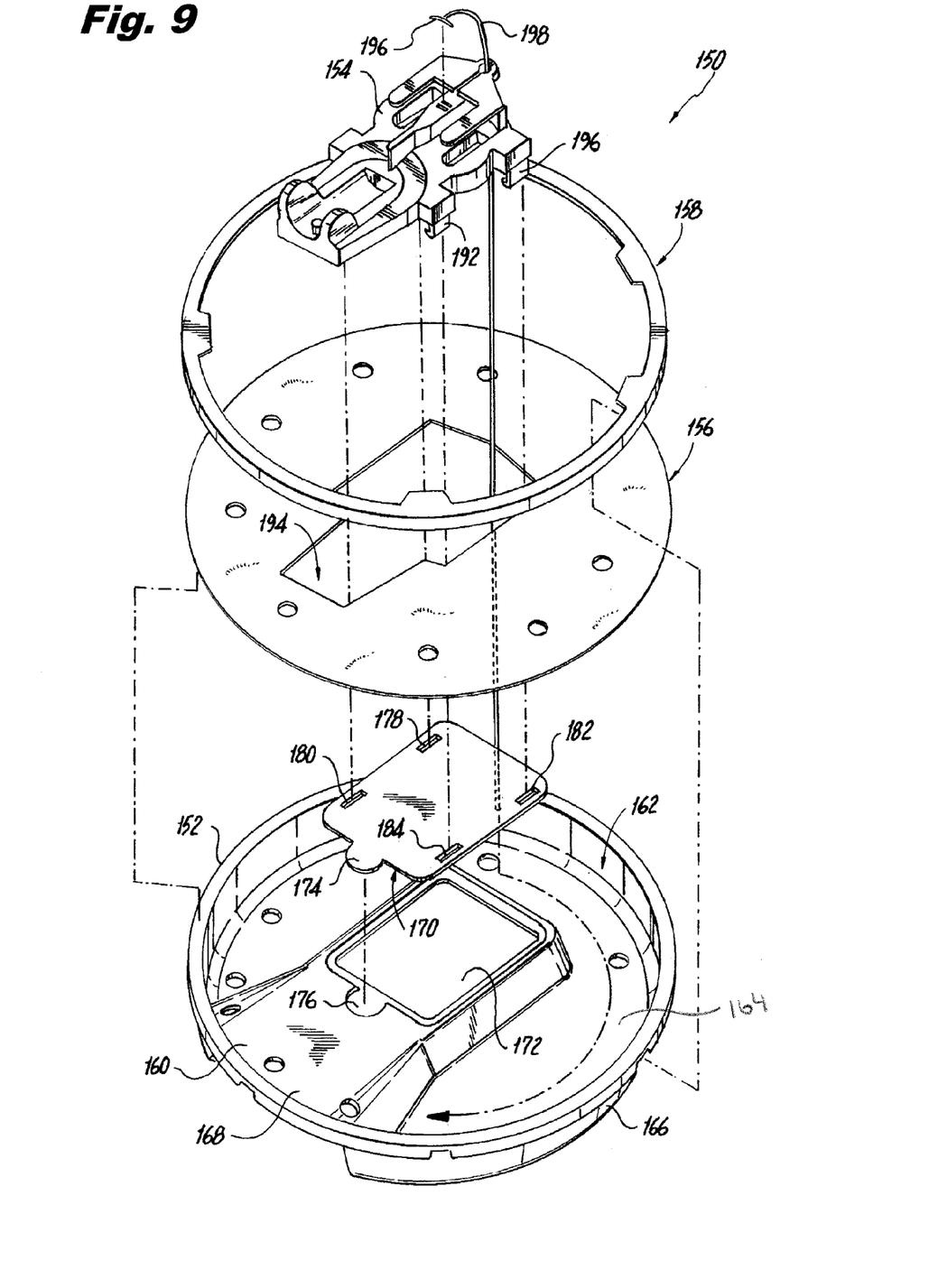
FIG. 9 is an exploded perspective view of another embodiment of a knotless suture package.

Refer now to FIG. 9, there is disclosed an alternative embodiment of a suture package 150 for use with a surgical suturing apparatus such as, for example, surgical suturing apparatus 112 described herein above. Suture package 150 is substantially identical to suture package 10 described herein above and generally includes a circular body portion 150 having a loading unit 154 mounted thereon. A cover 156 is provided to overlie circular body portion 152 and is secured to circular body portion 152 by a securing ring 158 in a substantially identical manner described hereinabove with regard to securing ring 18 and body portion 12 of suture package 10.

Body portion 152 also includes an inwardly directed tunnel 160 defining a U-shaped suture tray 162 within body portion 152. Body portion 152 includes a base 164 and a sidewall 166. Similar to tunnel 20 described herein above, tunnel 160 includes a tunnel top 168. Suture package 150 differs from suture package 10 described herein above in that loading unit 154 is not directly at attached to tunnel 160 but, rather, is attached to an intermediary plate 170. Intermediary plate 170 is positioned relative to a tunnel opening 172 formed in tunnel top 168 of tunnel 160. While intermediary plate 170 is illustrated as being above tunnel opening 172, it is contemplated that intermediary plate 170 may be positioned beneath tunnel opening 172 in tunnel 160.

In order to properly position intermediary plate 170 over tunnel opening 172, plate 170 is provided with an alignment tab 174 which is configured to be received within an alignment slot 176 formed in tunnel top 168.

In this embodiment, loading unit 154 is directly affixed to plate 170. Thus, plate 170 is provided with slots 178, 180, 182 and 184 which are configured to receive respective tabs 186 and 188 (not shown) and tabs 190 and 192 formed on loading unit 154. A cut out 194 formed in cover 156 provides clearance for tabs 186, 188, 190 and 192. Loading unit 154 is configured and functions in identical manner to loading unit 14 described herein above to supply a surgical needle 196 having a length of a barbed suture 198 attached thereto to surgical suturing apparatus 112.

Figure 10:
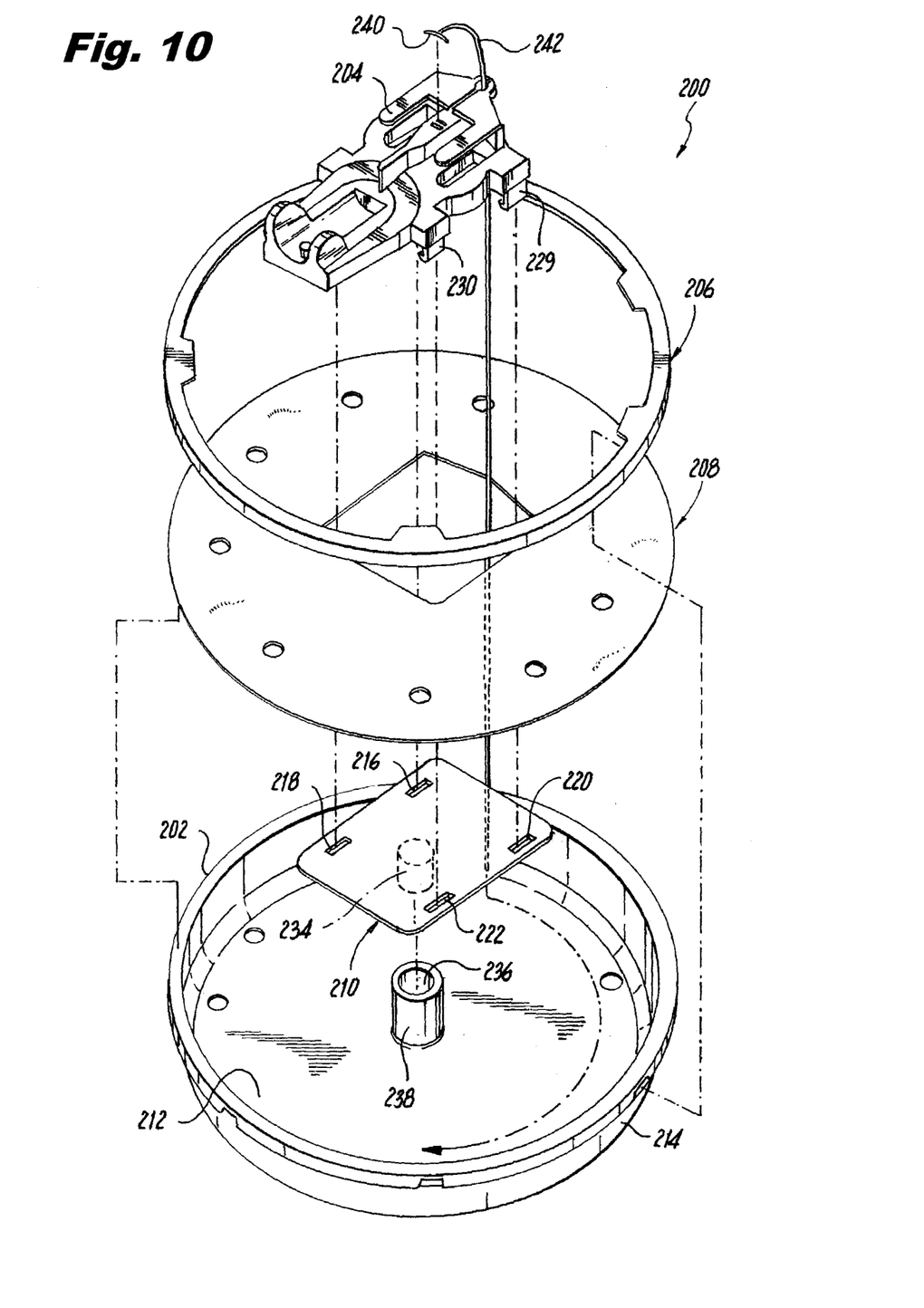
FIG. 10 is an exploded perspective view of still another embodiment of a knotless suture package.

Referring now to FIG. 10, there is disclosed a still further embodiment of a suture package 200. Similar to those embodiments described herein above, suture package 200 generally includes a circular body portion 202, a loading unit 204, a cover 208 and a ring 206 securing cover 208 to circular body portion 202. However, unlike those embodiments described herein above, circular body portion 202 does not include an inwardly directed tunnel. A plate 210 is provided to secure loading unit 204 to circular body portion 202. Loading unit 204 is substantially identical to those loading unit's described herein above and cover 208 is secured to body portion 202 by ring 206 in identical manner to that described herein above.

Body portion 202 includes a body portion based 212 and body portion sidewall 214. In order to secure loading unit 204 to plate 210, plate 210 is provided with slots 216, 218, 220 and 222 which are configured to receive and engage respective tabs 224 and 226 (not shown) and tabs 229 and 230 formed on loading unit 204 and in a manner substantially identical to that described herein above with regard to loading unit 154 and plate 170 in suture package 150.

Since body portion 202 does not include a tunnel, plate 210 is secured to base 212 of body portion 202. Specifically, a downwardly extending stud 234 extends from plate 210 and is secured within a bore 236 of an upwardly projecting tube 238. Tube 238 extends upwardly from base 212 of body portion 202. Stud 234 may be secured within tube 238 in any known manner such as, for example, gluing, welding, in friction fit fashion, etc.

Suture package 200 thus provides an alternative device for supplying a surgical needle 240 having a length of barbed suture material 242 attached thereto to surgical instrument 112.

Figure 11:
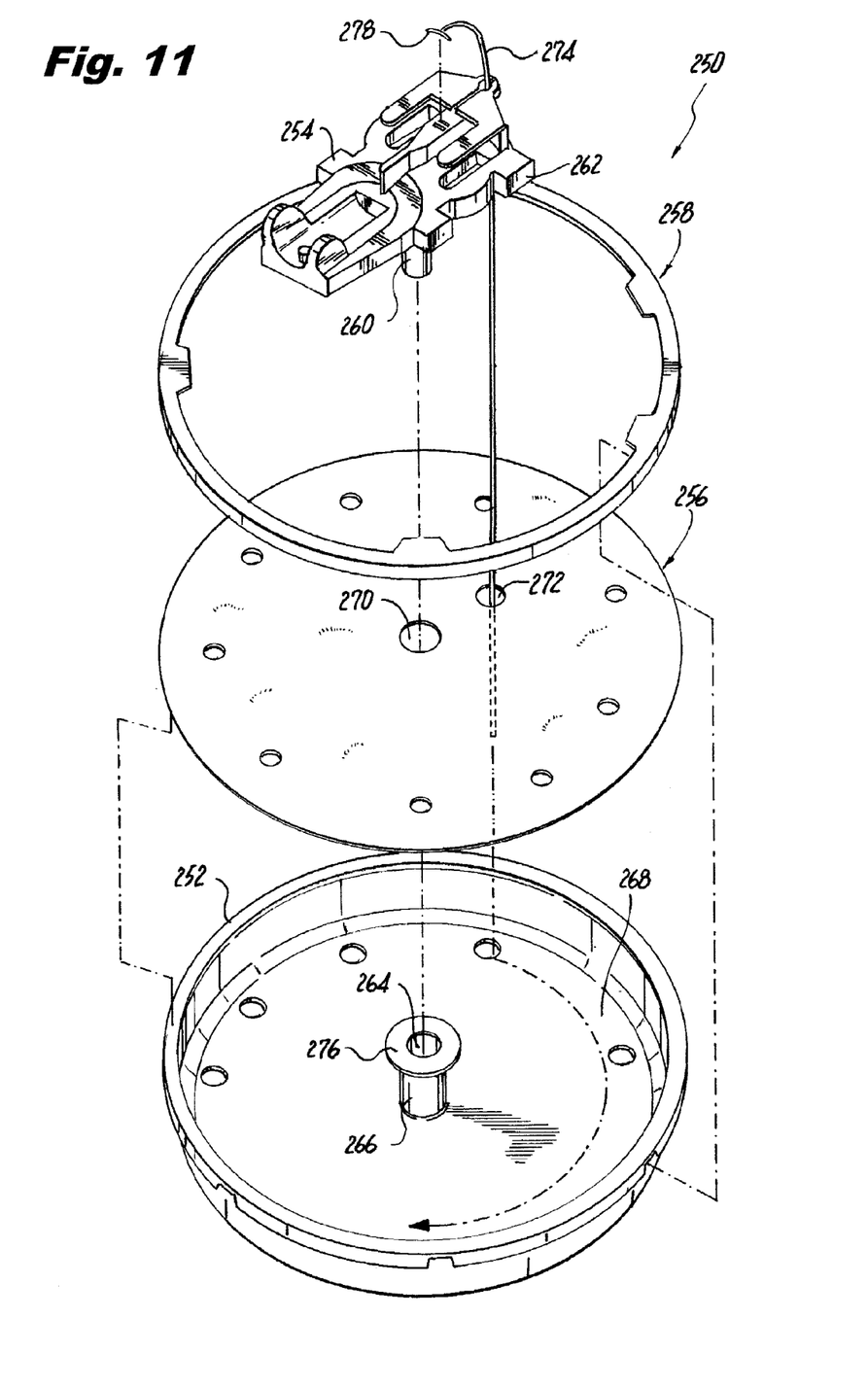
FIG. 11 is an exploded perspective view of yet another embodiment of a knotless suture package.

Referring to FIG. 11, there is disclosed a still further embodiment of a suture package 250. As with previous embodiments, suture package 250 generally includes a circular body portion 252, a loading unit 254, a cover 256 and a ring 258 securing cover 256 over circular body portion 252. These components function and assembled together and substantially identical manner to that described herein above with regard to the prior embodiments. However, in this particular embodiment, suture package 250 includes neither a tunnel nor a plate to secure loading unit 254 to circular body portion 252.

In this embodiment, a stud 260 extends downwardly from a base 262 of loading unit 254. Stud 260 is provided to be received within a bore 264 of a tube 266 extending upwardly from a base 268 of body portion 252. As with the prior embodiment, stud 260 may be secured within bore 264 in any known manner such as, for example, gluing, welding, friction fit fashion, etc. Since this embodiment does not include a tunnel or a plate, cover 256 does not need a substantial opening for tabs provided on loading unit 254. Cover 256 is provided with a first hole 270 for passage of stud 260. Similarly, cover 256 is provided with a second hole 272 for passage of a length of suture material 274. In order to stabilize loading unit 254 relative to body portion 252, tube 266 is provided with a flange 276 which supports base 264 of loading unit 254.

Thus, suture package 250 provides an alternative device for supplying a surgical needle 278, having length of suture material 274 attached thereto, to surgical suturing apparatus 112.

It will be understood that various modifications may be made to the embodiments disclosed herein. For example, the disclosed loading unit may be formed integrally with the body portion. Further, due to the large size of the disclosed suture tray, the disclosed suture packages may be configured to accommodate more than one loading unit. Additionally, multiple needle suture combinations may be provided in combination with the disclosed suture packages. Still further, and as noted hereinabove, the disclosed suture packages need not have a circular configuration but many assume other shapes. Therefore, the above description should not be construed as limiting, but merely as exemplifications of particular embodiments. Those skilled in the art will envision other modifications within the scope and spirit of the claims appended hereto.

The invention claimed is:

1. A suture package comprising:
a length of suture material;
a body portion defining a suture tray configured to support the length of suture material;
a loading unit disposed within the confines of the body portion, the loading unit being configured to support a surgical needle affixed to a proximal end of the length of suture material, wherein the loading unit is secured to the body portion; and
a cover removably secured between the body portion and the loading unit to retain the length of suture material within the suture tray, wherein the cover includes an opening through which the loading unit is received when the cover is secured to the body portion, wherein the proximal end of the length of suture material extends through the opening in the cover.

2. The suture package as recited in claim 1, wherein the body portion defines a tunnel extending inwardly toward a center of the body portion.

3. The suture package as recited in claim 2, wherein the loading unit is secured to the tunnel.

4. The suture package as recited in claim 3, wherein the loading unit includes tabs and the tunnel includes slots such that the loading unit is secured to the tunnel by engagement of the tabs within the slots.

5. The suture package as recited in claim 1, wherein the cover is removably secured to the body portion.

6. The suture package as recited in claim 5, wherein the loading unit is secured to the cover.

7. The suture package as recited in claim 5, further comprising a fixture positionable about the cover and engageable with the body portion to secure the cover to the body portion.

8. The suture package as recited in claim 5, further comprising a ring positionable about the cover and engageable with the body portion to secure the cover to the body portion.

9. The suture package as recited in claim 1, wherein the loading unit defines a gap for receiving the proximal end of the length of suture material from the suture tray.

10. The suture package as recited in claim 1, wherein the surgical needle is supported on the loading unit.

11. The suture package as recited in claim 1, wherein the body portion includes a plurality of inwardly extending tabs for selectively securing the cover to the body portion.

* * * * *